United States Patent [19]

Achord et al.

[11] Patent Number: 5,336,816
[45] Date of Patent: Aug. 9, 1994

[54] METHOD FOR PREPARING 1,1-DICHLORO-1-FLUOROETHANE

[75] Inventors: Betty J. Achord; C. Bradford Boyce, both of Baton Rouge, La.

[73] Assignee: Laroche Chemicals, Inc., Baton Rouge, La.

[21] Appl. No.: 992,146

[22] Filed: Dec. 17, 1992

[51] Int. Cl.$^5$ .............................................. C07C 17/08
[52] U.S. Cl. ..................................... 570/168; 570/166
[58] Field of Search ................................ 570/166, 168

[56] References Cited

U.S. PATENT DOCUMENTS

| | | |
|---|---|---|
| 2,894,044 | 7/1959 | Prill . |
| 4,209,470 | 6/1980 | Lorquet . |
| 4,766,258 | 8/1988 | Komatsu . |
| 4,948,479 | 8/1990 | Brooks et al. . |
| 4,950,364 | 8/1990 | Wismer . |
| 4,962,244 | 10/1990 | Elsheikh . |
| 4,975,156 | 12/1990 | Wismer . |
| 4,996,378 | 2/1991 | Wright et al. . |
| 5,008,474 | 4/1991 | Wairaevens et al. ............. 570/166 |
| 5,095,158 | 3/1992 | Bolmer . |

FOREIGN PATENT DOCUMENTS

| | | | |
|---|---|---|---|
| 2739478 | 3/1978 | Fed. Rep. of Germany ...... 570/166 |
| 58-217403 | 12/1983 | Japan . |
| 627773 | 8/1949 | United Kingdom . |

*Primary Examiner*—Alan Siegel
*Attorney, Agent, or Firm*—Jones, Day, Reavis & Pogue

[57] ABSTRACT

A more efficient reaction mechanism is provided for producing 1,1-dichloro-1-fluoroethane (HCFC-141b) by reacting vinylidene chloride with hydrogen fluoride in the liquid phase in the presence of a catalyst and sulfone-based or nitrated solvent. In particular, by using a titanium tetrafluoride catalyst in conjunction with tetramethylene sulfone solvent, most all the vinylidene chloride reagent can be converted to HCFC-141b to the virtual exclusion of unwanted, closely associated byproducts like 1,1-difluoro-1-chloroethane (HCFC-142b) 1,1,1-trifluoroethane (HFC-143a), while reducing the production of tars to a minimum.

20 Claims, No Drawings

METHOD FOR PREPARING 1,1-DICHLORO-1-FLUOROETHANE

BACKGROUND OF THE INVENTION

The present invention relates generally to the production of hydrogen chlorinated fluorocarbons (HCFC's), and more specifically to a method for preparing 1,1-dichloro-1-fluoroethane also known in the trade as HCFC-141b or R-141b.

Because of the celebrated ozone-depleting properties of chlorinated fluorocarbons (CFC's), they are falling out of favor for such uses as solvents for cleaning circuit boards, blowing agents for the extrusion of polymer foams, and aerosol propellants. Indeed, international treaties have established strict schedules for phasing out the use of CFC's.

HCFC's have been found to exhibit a relatively low ozone depletion potential, and have therefore been offered as a significant alternative to the use of CFC's. They include HCFC-141b, as well as the closely related 1,1-difluoro-1-chloroethane (a.k.a., HCFC-142b) and 1,1,1-trifluoroethane (a.k.a., HCFC-143a).

HCFC-141b has been prepared by a number of known methods. For example, 1,1,1-trichloroethane may be reacted with hydrogen fluoride as follows:

$$H_3C-\underset{\underset{Cl}{|}}{\overset{\overset{Cl}{|}}{C}}-Cl + H^+F^- \longrightarrow H_3C-\underset{\underset{Cl}{|}}{\overset{\overset{Cl}{|}}{C}}-F + HCl$$

to induce a halogen exchange between the chlorine and fluorine anions. U.S. Pat. No. 3,833,676 issued to Rokuo Ukaji et al. discloses such a reaction without the use of a catalyst, while U.S. Pat. No. 4,091,043 issued to Ohsaka et al., and European Published Application No. 353,059 issued to E.I. duPont de Nemours teach the use of metal halide catalysts, including antimony pentachloride. However, this halogen exchange reaction sequence suffers from several significant problems. First, for each molecule of HCFC-141b produced, a corresponding molecule of HCl is generated, which must be recovered and disposed of. Second, the trichloromethyl group of 1,1,1-trichloroethane reacts so readily in the halogen exchange reaction that multiple fluorination almost always occurs under normal operating conditions, thereby producing:

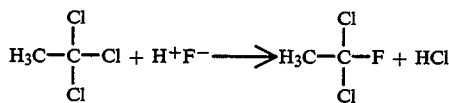

at the expense of the desired HCFC-141b product. This reduces significantly the yield of HCFC-141b, and poses the need to separate the unwanted HCFC-142b and HCFC-143a from HCFC-141b.

While E. T. McBee et al, "Fluorinated Derivatives of Ethane," *Industrial and Engineering Chemistry* (Mar. 1947), pp. 409–12 is directed to a method of producing HCFC-143a from either 1,1,1-trichloroethane or vinylidene chloride, the article also indicates that large amounts of HCFC-142b can be generated at high reaction temperatures and times as a side product. However, it also shows that no HCFC-141b was isolated.

It is known, however, that vinylidene chloride will react directly with HF to produce HCFC-141b without the generation of HCl, as follows:

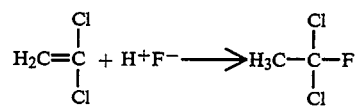

For example, U.K. Patent No. 627,773 issued to Chapman used stannic chloride at 35° C. for 1.75 hours to catalytically induce the reaction sequence, and convert 32.7% of the vinylidene chloride to HCFC-141b. A. L. Henne et al., "The Addition of Hydrogen Fluoride to Halo-Olefins," *Journal of American Chemical Society* (1943), vol. 65, pp. 1271–72, discloses a reaction at 65° C. for 3 hours, using 4 moles of HF without a catalyst to yield a product comprising 50% HCFC-141b, a trace of HCFC-142b, 10% unreacted vinylidene chloride, 5% CH$_3$CCl$_3$ (a.k.a., R-140), and 15% tar. Twenty percent of the product stream composition is unaccounted for. These procedures, however, give poor to moderate selectivity and conversion to HCFC-141b with relatively large amounts of tar. Indeed, the propensity of vinylidene chloride to dimerize and polymerize, as well as to over-fluorinate as in the halogen exchange mechanism, makes this route appear unattractive.

Efforts have also been made with varying degrees of success to use a vapor phase process for reacting vinylidene chloride with HF to produce HCFC-141b. U.S. Pat. No. 3,755,477 issued to Firth et al. discloses the use of a steam-treated chromium oxide catalyst at 80° C. to yield 46% HCFC-141b, the remainder being unwanted fluorinated products like HCFC-142b and HFC-143a. At 90°–100° C., however, no HCFC-141b was produced. U.S. Pat. No. 3,803,241 issued to Stolkin used alumina impregnated with a chromium salt solution at 198° C. to catalytically induce a vapor-phase reaction producing 98.8% HFC-143a and 0.2% each of HCFC-141b and HCFC-142b. By contrast, European Published Application No. 353,059 issued to E.I. duPont de Nemours teaches a process passing the reagents mixed in the vapor phase through an aluminum fluoride catalyst at 74°–86° C. using a molar HF/vinylidene chloride ratio of 4.3 to produce a product stream comprising 99.8% HCFC-141b, 0.1% HCFC-142b, and 0.1% unreacted vinylidene chloride with an 89.6% yield. The missing 10% of the product stream is probably tar, which would shorten the life of the catalyst.

Vinylidene chloride has also been reacted with HF in the liquid phase to produce HCFC-142b, as disclosed by Japanese Published Application No. 47-39086 issued to Kureha Kagaku Kogyo Co., Ltd., using a stannous chloride catalyst. Running the process at 90° C. for 60 minutes using a 6.0 HF/vinylidene chloride ratio, 96.4% of the vinylidene chloride reagent was converted to fluorochloroethanes, for a yield of 76.4% HCFC-142b, 8.0% HCFC-141b, and 12.0% HFC-143a—a high conversion rate, but an exceedingly low yield of HCFC-141b product. The disclosure also indicates that when TiCl$_4$ catalyst was used, 40.4% of the resulting product stream comprised HCFC-141b, while HCFC-142b accounted for 4.0%. However, identifiable organic products only accounted for 51% of the product stream leaving 49% for tar. The moderate yield of HCFC-141b product and large production of tar makes this process undesirable.

SUMMARY OF THE INVENTION

Accordingly, it is an object of the present invention to provide a method, which converts vinylidene chloride and HF to HCFC-141b.

Another object of the present invention is to provide such a method, which selectively produces HCFC-141b, with minimal formation of HCFC-142b, tar, and other undesirable byproducts.

Yet another object of the present invention is to provide such a method, which converts a large percentage of the vinylidene chloride to organic products.

Still another object of the present invention is to increase production of the HCFC-141b end product by providing a method which requires a relatively short reaction time period.

Yet another object of the present invention is to use reagents in the liquid phase for such a reaction in order to reduce reactor volumes and energy consumption levels required for the process.

Other objects of the invention, in addition to those set forth above, will become apparent to those skilled in the art from the following invention disclosure.

Briefly, the invention is directed to providing a more efficient reaction mechanism for producing HCFC-141b by reacting vinylidene chloride with hydrogen fluoride in the liquid phase in the presence of a catalyst and sulfone-based or nitrated. In particular, by using a titanium tetrafluoride catalyst in conjunction with tetramethylene sulfone solvent, most all the vinylidene chloride reagent can be converted to HCFC-141b to the virtual exclusion of unwanted, closely associated byproducts like HCFC-142b and HFC-143a, while reducing the production of tars to a minimum.

DETAILED DESCRIPTION OF THE PREFERRED EMBODIMENT

The preferred catalyst for converting vinylidene chloride to HCFC-141b using an excess of HF is titanium tetrafluoride ($TiF_4$), although titanium may be conveniently added as a tetrahalide, or another $Ti^{+4}$ derivative like titanium tetrachloride ($TiCl_4$), which will be readily converted to $TiF_4$ in the presence of anhydrous HF. Catalysts like boron trifluoride etherate ($BF_3$) and tin tetrachloride ($SnCl_4$) may also be used, although $BF_3$ is highly volatile, and therefore is readily lost from the reactor.

The preferred solvent for the catalyst/solvent system is a sulfone, preferably tetramethylene sulfone, also known as sulfolane:

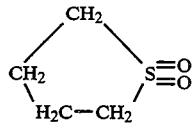

Any other sulfones that are stable to HF and the catalyst, having a melting point below 60° C. in the presence of HF, such as dimethyl sulfone, may also be used, however. Nitrated solvents like nitromethane or nitrobenzene likewise modify the activity of $TiF_4$, and may be also used to good effect.

The catalyst/solvent system is prepared by dissolving and suspending the titanium compound in the solvent, and treating the mixture with excess anhydrous HF. While $TiCl_4$ comprises the titanium source of the preferred embodiment, $TiO_2$ or titanium tetra-alkoxide may be used if a drying agent like thionyl chloride is employed to destroy the water or alcohol formed thereby. The resulting catalyst is soluble in the solvent, and forms a complex with it.

The molar ratio of solvent to catalyst may range between 2 and 50, the preferred ratio being between 6 and 9.5. Lower ratios result in higher carbonation and tar formation, while high ratios lead to reduced reaction rates.

The molar ratio of vinylidene chloride to catalyst may range between 10 and 200, the preferred ratio being 20. The lower ratios result in greater byproduct formmnation, while the higher ratios provide unnecessarily slow reaction rates.

Excess HF is necessary to drive the reaction to high conversion. While a 2-to-3 molar excess with respect to the vinylidene chloride reagent is preferred, larger excesses may be used to advantage.

Reaction temperatures may range between 25° C. and 150° C. with the preferred temperature being 60°–95° C. Pressure is not a critical element of the reaction. Since autogenous pressure is most convenient, it is preferred. It is preferred to run the reaction as a continuous process.

EXAMPLES

The reactions were analyzed using a Hewlett-Packard 5890 gas chromatograph with thermal conductivity detectors, using a 30-foot, 0.5 mm, DB-1 megabore capillary column. Peaks were identified with a Hewlett-Packard 5971A mass selective detector.

The experiments were run in a 300 ml stirred Hastaloy C Parr autoclave fitted with a thermocouple and pressure gauge. In the bomb were placed sulfolane and $TiCl_4$ or anhydrous $TiF_4$. The bomb was sealed and weighed. A weighed quantity of HF was then added through a dip tube at room temperature. A moderate exotherm from the solvation of HF in the sulfolane was observed. When $TiCl_4$ was used, pressure built up in the reactor from liberation of HCl.

Next, the bomb was cooled to about 10° C. When HCl was present, the bomb was vented and reweighed. To the cold mixture was added 81 ml (i.e., 97 g or 1 mole) of vinylidene chloride through the gas inlet by means of a syringe. The bomb was then placed in a preheated bath fitted with a temperature controller, and brought to the desire temperature as rapidly as possible, and maintained thereafter at that temperature.

Immediately after the desired temperature was reached, and periodically thereafter until the reaction was complete, a vapor sample was withdrawn by attaching a 50 ml polyethylene syringe containing 1–2 g of crystalline trisodium phosphate to the gas outlet. The syringe was capped and shaken until the HF was neutralized. The vapor sample was then analyzed by gas chromatography. The sampling times were then adjusted to take into account the reaction that took place during the heatup period, and to provide the best fit of the rate constant K for the reaction. The K values thus obtained were subjected to regression analysis, and are reported in Table 1.

The yield of crude HCFC-141b was determined by distilling the volatiles from the bomb at 60°–70° C. through a dry ice-cooled condenser into a teflon-coated separatory funnel cooled in an ice bath. The upper layer comprised HF, while the lower layer comprised HCFC-141b. The HCFC-141b fraction was separated, washed with water, dried over anhydrous, potassium carbonate, and weighed. Due to the volatility of the HCFC-141b and the HCFC-141b/HF azeotrope, and the solubility of HCFC-141b in liquid HF, there were significant losses of the product during workup. Yields of HCFC-141b in the total volatile organic product determined by gas chromatography and isolated crude yields (usually greater than 97% pure by GC) are reported in Table 1.

After stripping the volatiles, the bomb was weighed once again to determine the amount of HF retained by the sulfolane. This mixture was reused in successive runs until a new catalyst level was required, or the bomb seals failed.

Average volatile "tars" were estimated by combining the crude HCFC-141b from a series of runs at a single catalyst level, and distilling the HCFC-141b through an efficient packed distillation column. The pot residue was weighed, and that weight divided by the total number of runs is reported in Table 2.

Average nonvolatile tars were estimated by pouring the stripped sulfolane/HF catalyst residue left in the bomb after a series of runs at the same catalyst level on ice and 100 ml of 20% aqueous HCl. The mixture was then extracted three times with methylene chloride, and the aqueous layer discarded. The combined organic extract was washed three times with 10% aqueous HCl, three times with concentrated sulfuric acid, dried over anhydrous potassium carbonate, and filtered and evaporated on a Rotovap at atmospheric pressure and 60° C. The residue was weighed, divided by the number of runs represented, and reported in Table 2.

Thus, it can be seen that when sulfolane was not used, only 50-79% of the product stream comprised identified organic materials, the remainder being tar, although all but 1% of the vinylidene chloride was reacted. The reaction was relatively selective, with 73.1-95.3% of the product stream comprising HCFC-141b. By adding sulfolane to modify the titanium-based catalyst, however, conversions consistently ranging between 83% and 95% were obtained with HCFC-141b accounting for 95.0-98.7% of the volatile components contained in the product stream. Not only was the reaction highly selective in favor of HCFC-141b to the virtual exclusion of HCFC-142b with almost complete conversion of the vinylidene chloride reagent, but also short reaction times and relatively low temperatures were used.

TABLE 1

| Example | Initial HF (Moles) | Catalyst (Mole %) | Sulfolane (ml) | Temperature (°C.) | Rate K2 | Reaction Time (minutes) | Percent Conversion to Volatile Products | Losses* | Percent Volatile Product Fraction | | |
|---|---|---|---|---|---|---|---|---|---|---|---|
| | | | | | | | | | Vinylidene chloride | HCFC-141b | HCFC-142b |
| 1 | 3.35 | 5.0 | 0 | 47 | 0.0313 | 47 | 50 | 50 | 0.6 | 73.1 | 26.3 |
| 2 | 3.16 | 5.0 | 0 | 51 | 0.0408 | 29 | 79 | 21 | 1.0 | 95.3 | 3.7 |
| 3 | 3.94 | 5.0 | 12.5 | 48 | 0.0559 | 51 | 85 | 15 | 1.2 | 98.7 | 0.1 |
| 4 | 2.95 | 5.0 | 12.5 | 54 | 0.0579 | 50 | 83 | 17 | 1.3 | 98.5 | 0.2 |
| 5 | 4.02 | 5.3 | 25 | 60 | 0.0727 | 32 | 89 | 11 | 1.1 | 97.6 | 1.3 |
| 6 | 3.84 | 5.4 | 50 | 45 | 0.0491 | 45 | 89 | 11 | 1.8 | 96.1 | 2.1 |
| 7 | 4.60 | 5.4 | 50 | 50 | 0.0682 | 33 | 87 | 13 | 1.5 | 96.6 | 1.9 |
| 8 | 3.85 | 5.4 | 50 | 50 | 0.0714 | 53 | 83 | 17 | 0.9 | 97.1 | 2.0 |
| 9 | 3.89 | 2.0 | 50 | 55 | 0.1617 | 51 | 95 | 5 | 0.6 | 98.4 | 1.0 |
| 10 | 3.57 | 1.0 | 50 | 55 | 0.1790 | 92 | 85 | 15 | 1.6 | 97.6 | 0.8 |
| 11 | 4.18 | 1.0 | 50 | 55 | 0.2324 | 55 | 92 | 8 | 0.7 | 98.4 | 0.9 |
| 12 | 4.04 | 0.5 | 50 | 55 | 0.2623 | 81 | 89 | 11 | 2.7 | 96.5 | 0.8 |
| 13 | 3.98 | 5.4 | 50 | 60 | 0.1053 | 27 | 85 | 15 | 0.5 | 98.2 | 1.3 |
| 14 | 3.97 | 2.0 | 50 | 65 | 0.1884 | 50 | 92 | 8 | 1.5 | 97.0 | 1.5 |
| 15 | 3.46 | 1.0 | 50 | 65 | 0.2084 | 85 | 80 | 20 | 1.0 | 97.9 | 1.1 |
| 16 | 3.68 | 2.0 | 50 | 65 | 0.2577 | 38 | 91 | 9 | 0.7 | 97.9 | 1.6 |
| 17 | 3.52 | 1.0 | 50 | 65 | 0.3214 | 71 | 92 | 8 | 0.6 | 97.9 | 1.5 |
| 18 | 4.17 | 5.4 | 50 | 69 | 0.2457 | 27 | 89 | 11 | 0.5 | 95.0 | 4.5 |

*These are materials that under the particular laboratory conditions were not collectable. They were primarily organic product, due to the high volatility thereof, with some tar.

TABLE 2

| Catalyst (Mole %) | Sulfolane (ml) | No. batch runs averaged[1] | Total amount of nonvolatile tar (g) | Total amount of volatile tar (g) | Average amount tar per batch run (g) | Total tars (wt. %) |
|---|---|---|---|---|---|---|
| 0.5 | 50 | 8 | 1.2 | | 0.2 | |
| | | 7 | | 18.1 | 2.6 | 2.9 |
| 1.0 | 50 | 8 | 3.1 | | 0.4 | |
| | | 8 | | 19.2 | 2.4 | 2.9 |
| 2.0 | 50 | 8 | 3.1 | | 0.4 | |
| | | 8 | | 14.1 | 1.8 | 2.2 |
| 5.4 | 50 | 8 | 2.4 | | 0.3 | |
| | | 8 | | 15.3 | 1.9 | 2.3 |
| 5.3 | 25 | 10 | 4.4 | | 0.4 | |
| | | 10 | | 20.6 | 2.1 | 2.6 |
| 5.0 | 12.5 | 4 | * | | — | |
| | | 4 | | 10.8 | 2.7 | 3.5[2] |
| 5.0 | 0 | 4 | large * | | 5? | |

TABLE 2-continued

| Catalyst (Mole %) | Sulfolane (ml) | No. batch runs averaged[1] | Total amount of nonvolatile tar (g) | Total amount of volatile tar (g) | Average amount tar per batch run (g) | Total tars (wt. %) |
|---|---|---|---|---|---|---|
| | | 4 | | 11.5 | 1.9 | 4.5–6.0[2] |

*Semi-solid residue which formed a stable emulsion on workup.
[1] While the catalyst and sulfolane solvent in the reactor were reused between batch runs, additional vinylidene chloride and hydrogen fluoride reagents were introduced for each run.
[2] These are conservative estimates.

What is claimed is:

1. A method for preparing 1,1-dichloro-1-fluoroethane (HCFC-141b) in high yield, comprising reacting vinylidene chloride and hydrogen fluoride in the presence of a catalyst and a solvent selected from the group consisting of tetramethylene sulfone, dimethyl sulfone, nitromethane, and nitrobenzene.

2. A method for preparing HCFC-141b as recited in claim 1, wherein the catalyst comprises a tetrahalide of titanium or another derivative of titanium having a +4 valence state.

3. A method for preparing HCFC-141b as recited in claim 2, wherein the catalyst comprises titanium tetrafluoride.

4. A method for preparing HCFC-141b as recited in claim 2, wherein the catalyst comprised titanium tetrachloride.

5. A method for preparing HCFC-141b as recited in claim 1, wherein the catalyst comprises boron trifluoride etherate.

6. A method for preparing HCFC-141b as recited in claim 1, wherein the catalyst comprises tin tetrachloride.

7. A method for preparing HCFC-141b as recited in claim 1, wherein the molar ratio of solvent-to-catalyst ranges between 2 and 50.

8. A method for preparing HCFC-141b as recited in claim 7, wherein the molar ratio of solvent-to-catalyst ranges between 6 and 9.5.

9. A method for preparing HCFC-141b as recited in claim 1, wherein the molar ratio of vinylidene chloride-to-catalyst ranges between 10 and 200.

10. A method for preparing HCFC-141b as recited in claim 9, wherein the molar ratio of vinylidene chloride-to-catalyst comprises about 20.

11. A method for preparing HCFC-141b as recited in claim 1, wherein the molar ratio of hydrogen-fluoride-to-vinylidene chloride is at least 1.

12. A method for preparing HCFC-141b as recited in claim 11, wherein the molar ratio of hydrogen fluoride-to-vinylidene chloride is about 2-5.

13. A method for preparing HCFC-141b as recited in claim 1, further comprising a reaction temperature of about 25°–150° C.

14. A method for preparing HCFC-141b as recited in claim 13, wherein the reaction temperature is about 60°–70° C.

15. A method for preparing HCFC-141b as recited in claim 1, wherein the vinylidene chloride and hydrogen fluoride reagents are reacted in the liquid phase.

16. A method for preparing HCFC-141b as recited in claim 1, wherein at least 80% of the vinylidene chloride reagent is converted to volatile organic materials.

17. A method for preparing HCFC-141b as recited in claim 16, wherein the portion of the volatile organic materials comprising unreacted vinylidene chloride is less than 3%.

18. A method for preparing HCFC-141b as recited in claim 16, wherein the portion of volatile organic materials comprising HCFC-141b is at least about 90%.

19. A method for preparing HCFC-141b as recited in claim 16, wherein the portion of the volatile organic materials comprising 1,1-difluoro-1-chloroethane (HCFC-142b) is less than about 5%.

20. A method for preparing HCFC-141b as recited in claim 1, wherein the portion of the end product comprising tar is less than 5% by weight.

* * * * *